(12) United States Patent
Guarino

(10) Patent No.: US 12,337,014 B1
(45) Date of Patent: Jun. 24, 2025

(54) INTRACAVERNOSAL GEL INFUSION SYSTEM WITH NEUROTOXIN MODULATION FOR ERECTILE FUNCTION

(71) Applicant: Enrico Guarino, Burlington, MA (US)

(72) Inventor: Enrico Guarino, Burlington, MA (US)

( * ) Notice: Subject to any disclaimer, the term of this patent is extended or adjusted under 35 U.S.C. 154(b) by 0 days.

(21) Appl. No.: 18/745,659

(22) Filed: Jun. 17, 2024

(51) Int. Cl.
*A61K 35/16* (2015.01)
*A61K 9/00* (2006.01)
*A61K 38/48* (2006.01)

(52) U.S. Cl.
CPC ............ *A61K 35/16* (2013.01); *A61K 9/0034* (2013.01); *A61K 38/4893* (2013.01); *C12Y 304/24069* (2013.01)

(58) Field of Classification Search
CPC .. A61K 35/16; A61K 9/0034; A61K 38/4893; C12Y 304/24069
See application file for complete search history.

(56) References Cited

U.S. PATENT DOCUMENTS

| | | | |
|---|---|---|---|
| 6,071,272 A | 6/2000 | Hoffman et al. | |
| 8,329,193 B2 * | 12/2012 | Gaxiola | A61K 38/4893 424/239.1 |
| 9,764,010 B2 | 9/2017 | Nilsson Neijber | |
| 2011/0052636 A1 | 3/2011 | Gaxiola et al. | |
| 2012/0183519 A1 | 7/2012 | Swift | |
| 2018/0147111 A1 * | 5/2018 | Gaines | A61K 35/19 |
| 2019/0358266 A1 * | 11/2019 | Suescun, Jr. | A61K 47/46 |

OTHER PUBLICATIONS

Godoi et al. Platelet-Rich Plasma Gel Matrix (PRP-GM): Description of a New Technique. Bioengineering. 2022;9(12):817.*
Cowper et al. Penile Stretching as a Treatment for Peyronie's Disease: A Review. Sexual Medicine Reviews. 2019;7(3):508-515.*

* cited by examiner

*Primary Examiner* — Lynn Y Fan
(74) *Attorney, Agent, or Firm* — Sanchelima & Associates, P.A.; Jesus Sanchelima; Christian Sanchelima

(57) ABSTRACT

A method is provided for penile rejuvenation comprising a series of plasma gel and Dysport injections to restore youthful structure and function. Blood is drawn to isolate plasma, which is heated to produce a growth factor-rich gel. The gel is injected into the penis shaft for tissue volumization and into the cavernosa to improve erectile function. Dysport is additionally injected at the penile base to relax ligaments for improved length and into the glans to control prostate secretions. Benefits include enhanced size and fullness, better erectile strength, and reduced leakage. This non-surgical procedure offers a novel approach to aging male aesthetics and sexual dysfunction using the patient's own plasma and targeted chemodenervation with Dysport.

12 Claims, 1 Drawing Sheet

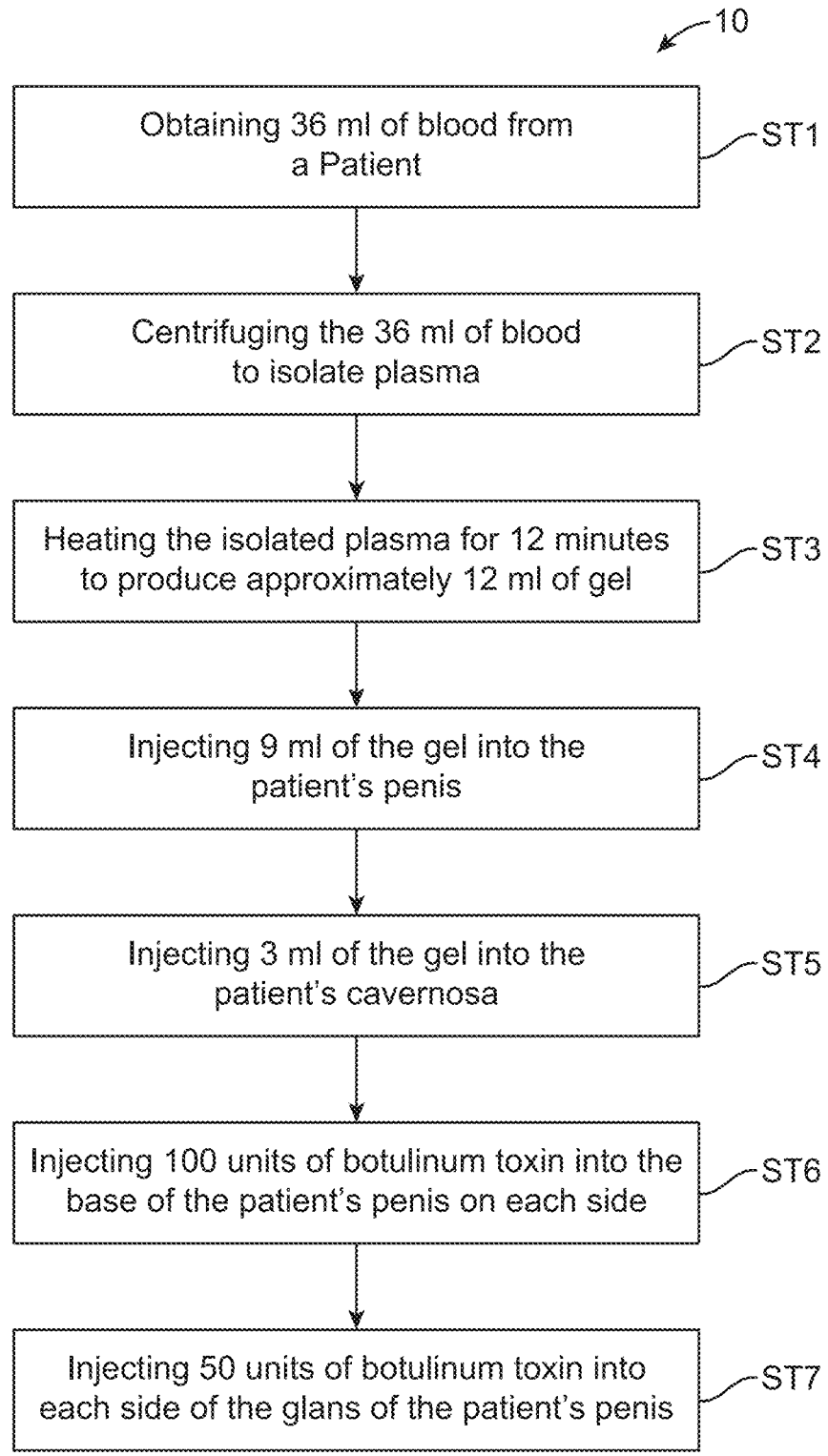

INTRACAVERNOSAL GEL INFUSION SYSTEM WITH NEUROTOXIN MODULATION FOR ERECTILE FUNCTION

BACKGROUND OF THE INVENTION

1. Field of the Invention

The present invention relates to a method for treating erectile dysfunction and, more particularly, to a method for treating erectile dysfunction that use of plasma-derived gel and targeted injection of Dysport/Botulinum toxin.

2. Description of the Related Art

Several designs for drugs and devices have been developed in the past for treating genital or sexual disorders and promoting penis erection. However, existing options have various limitations. Drugs may cause systemic side effects or lack efficacy for some patients. Mechanical erection aids do not treat the underlying cause and can have comfort or aesthetic issues. Surgical implants carry risks and complications. Recent advances utilize the patient's own platelet-rich plasma (PRP) and purified botulinum toxin injections to more effectively and safely improve erectile function, size, strength, and aesthetics. However, methods combining PRP gel infusion with strategic neurotoxin modulation in the cavernosa, penile base, and glans have not been explored. Therefore, there is a need for a refined approach that leverages autologous PRP therapy with targeted chemodenervation to achieve comprehensive penile rejuvenation. The present invention aims to address this need with a novel technique for treating erectile dysfunction and restoring youthful structure and function using the patient's own biological substances and precise tissue-specific injection methods.

Applicant believes that a related reference corresponds to U.S. patent publication No. 2019/0358266 disclosing compositions and methods are disclosed for treating erectile dysfunction in a patient. A sample of whole blood is collected from the patient, and a sample of platelet-rich plasma (PRP) is extracted from the sample of whole blood. The sample of PRP is mixed with a predetermined amount of botulinum toxin (BTX) to form a PRP/BTX mixture, which is then injected into a region of human tissue of the patient.

Applicant believes that another related reference corresponds to U.S. patent publication No. 2011/0052636 which relates to methods of treating premature ejaculation with a neurotoxin such as a botulinum toxin.

Applicant believes that U.S. Pat. No. 9,764,010 to Nilsson Neijber et al. is another related reference. Neijber teaches methods for treating premature ejaculation and prolongation of climax time in a patient in need thereof by local administration of a Clostridial neurotoxin, such as a botulinum toxin, are provided.

U.S. Pat. No. 6,071,272 to Alan S. Hoffman et al. teaches a method for treating erectile dysfunctionality by injecting pharmacological agents into the corpora cavernosa of the penis. The present invention employs an improved method for injecting pharmacological agents into the corpora cavernosa of the penis which does not require a hypodermic needle and the attendant problems associated with the use of hypodermic needles to inject pharmacological agents into the penis and to provide a new treatment option to many patients with erectile dysfunctionality.

U.S. Patent Publication No. 2012/0183519 to Matthew Swift teaches methods, apparatus, and compositions related to a method of treating erectile dysfunction in a subject, the method comprising administering a composition comprising platelet-rich plasma at or proximate to ischemic tissue comprising the corpora cavernosa or corpus spongiosum.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to improve erectile function—Direct injection of plasma gel into the cavernosa and Dysport® into the penile base can improve blood flow and strength of erections. This helps treat erectile dysfunction.

It is another object of this invention to provide improved penile length and positioning—Injecting botulinum toxin into the penile base can temporarily relax the fundiform and suspensory ligaments that anchor the penis, reducing inward pulling forces. This allows for improved penile length and a more forward, youthful positioning of the penis.

It is still another object of the present invention to provide a It is still another object of the present invention to provide enhanced penile glandular control and function—Injecting botulinum toxin into the glans penis reduces involuntary muscular contractions that can lead to undesired urethral discharge or leakage. This improves control over penile glandular secretions and promotes better overall penile hygiene and function.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a flow chart for a method.

DETAILED DESCRIPTION OF THE EMBODIMENTS OF THE INVENTION

Referring now to the drawings, where the present invention is generally referred to with numeral 10, it can be observed that it basically includes ST 1 to ST 7. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

In ST 1, approximately 36 ml of blood is obtained from the patient undergoing penile rejuvenation treatment. A standard venipuncture procedure is performed using a needle or catheter inserted into the patient's vein, typically in the arm. An appropriate anticoagulant is added to the collection container to prevent the blood from clotting. Once the desired 36 ml volume of blood has been collected in the container, the needle/catheter is removed from the patient's vein and standard pressure is applied to the puncture site to stop bleeding. The collected blood is gently mixed with the anticoagulant. The 36 ml volume of collected blood provides a sufficient quantity of plasma for isolation and preparation of the gel injection in subsequent steps of the method. Standard blood handling precautions are followed throughout the collection procedure.

In ST 2, the 36 ml of anticoagulated blood obtained in ST 1 is transferred to an appropriate centrifuge tube. The tube is placed into a centrifuge device and spun at a force of approximately 1500× g for 10 minutes. This separates the blood into its component parts based on density—the red blood cells settle at the bottom of the tube while the plasma, which has a lower density, settles above the red blood cells. The tube is then carefully removed from the centrifuge. Using a pipette, the upper plasma layer is withdrawn and transferred into a separate sterile tube, leaving the red blood cells behind. Approximately 12 ml of plasma is obtained following this process. The isolated 12 ml of plasma contains platelets and growth factors that will facilitate tissue regeneration and rejuvenation when re-injected into the penis. Standard precautions are followed to maintain sterility during the centrifugation process. The plasma is now ready for the heating step to prepare the gel for injection.

In ST 3, Heating the isolated plasma for 12 minutes produces approximately 12 ml of gel: The 12 ml of plasma isolated in the previous centrifugation step is transferred to a sterile glass tube or vial. The tube with the plasma is then placed in a laboratory heating block or water bath that is preheated to maintain a steady temperature of 55-60° C. The plasma is heated at this temperature range for approximately 12 minutes. Heating the plasma stimulates the release of growth factors from the platelets in the plasma and initiates the formation of a fibrin gel matrix. The temperature and duration are controlled to achieve partial coagulation of the plasma into a gel-like formulation. After 12 minutes, the plasma will have thickened into approximately 12 ml of gel with a honey-like consistency. The gel contains concentrated levels of platelet-derived growth factors and fibrin that will promote tissue volumization, rejuvenation and decreased inflammation when injected into the penis.

Standard laboratory procedures are followed to maintain proper heating conditions and prevent contamination during the heating process. The resulting 12 ml of growth factor-rich gel is now ready for injection in the subsequent steps outlined in the method claim.

In ST 4, the patient is properly prepped and positioned for the injection procedure. Using a standard small-gauge needle or cannula, 9 ml of the thermally-induced platelet-rich plasma gel prepared in the previous steps is carefully injected into specific areas of the patient's penis. Approximately 4.5 ml of the plasma gel is evenly injected bilaterally above the deep Buck's fascia, accessing the subcutaneous plane by inserting the needle at the 6 and 9 o'clock positions along the penile shaft and distributing the gel as the needle is withdrawn. This allows integration of the gel above the fascia to promote rejuvenation and shaping. The remaining 4.5 ml of plasma gel is used for injection into the cavernosa and gland's submucosa as described in ST 5.

In ST 5, approximately 4.5 ml of the previously prepared plasma gel is used for injection into specific areas of the cavernosa and gland. Using a fine needle, about 1.5 ml of the plasma gel is injected directly into each of the left and right cavernosa along the length from base to glans. This allows targeted delivery into the erectile tissues for rejuvenation. Additionally, using a small gauge needle, approximately 1.5 ml of the plasma gel is carefully injected into the gland's submucosal space. The gel is evenly distributed by making multiple small injections along the left and right sides of the glans. Precise injection technique is critical for avoiding vascular injury and damage to penile tissues. Injection of the gel promotes regeneration and restoration of erectile function and glandular control.

In ST 6, the base of the penis is precisely marked to identify injection sites on the left and right sides. Using a 30-gauge needle, 100 units of Dysport® (abobotulinumtoxinA) is carefully injected into the subcutaneous tissues on the left side of the penile base, distributed in small boluses. This is repeated, injecting another 100 units of abobotulinumtoxinA into the right side of the penile base. Dysport® is a purified botulinum toxin type A that causes temporary muscle relaxation when injected. Injecting abobotulinumtoxinA into the penile base muscles allows targeted relaxation of the fundiform and suspensory ligaments anchored to this area. This reduces inward pull on the penis for improved length and positioning. Precise injection technique is utilized to accurately deliver the abobotulinumtoxinA along the penile base. Care is taken to avoid injection into blood vessels. Temporary penile stretching maneuvers may be performed following abobotulinumtoxinA administration to enhance distribution within the target muscles. Effects typically become noticeable within 2-3 days as the abobotulinumtoxinA takes effect.

When the patient is prepped and the corpus cavernosum injection sites are identified. Using a 30 gauge needle, botulinum toxin (BTX) is injected bilaterally into the base and top of the corpus cavernosum as follows: Approximately 20 units of BTX is carefully inserted into the left corpus cavernosum at the base of the penis, distributing the dose evenly. This is repeated with another approximate 20 unit injection into the right corpus cavernosum at the penile base. Additionally, 20 units of BTX are slowly injected into the left proximal end of the corpus cavernosum approaching the glans. This is mirrored with another 20 unit injection into the right proximal corpus cavernosum.

In ST 7, The injection sites on the left and right sides of the glans (head) of the penis are precisely marked. Using a 30-gauge needle, 50 units of Dysport are injected into the subcutaneous tissues on the left side of the glans. Care is taken to evenly distribute the injections over the marked area. This process is repeated, injecting another 50 units of Dysport into the right side of the glans. Precise injection technique targets the Dysport to the submucosal glandular tissues. Injecting Dysport into the glans produces relaxation of the muscular fibers controlling glandular secretion into the urethral lumen. This reduces prostate secretions and involuntary leakage or discharge from the urethral orifice. Temporary light massage or compression may be applied to the glans following injection to assist with dispersion of Dysport within the glandular structure. The effects typically become noticeable in 2-3 days as the Dysport takes effect, improving penile glandular control and function.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:
1. A method for penile rejuvenation, comprising:
obtaining a blood sample from a patient;

isolating plasma from the blood sample by centrifuging at 1500× g for 10 minutes;

heating the isolated plasma for 12 minutes to produce a plasma gel;

injecting a first portion of the plasma gel into the penile shaft of the patient; wherein said first portion of the plasma gel is 9 ml injected into the subcutaneous plane above the deep Buck's fascia of the penile shaft by inserting a 30-gauge needle at the 6 and 9 o'clock positions along the penile shaft and distributing the plasma gel as the needle is withdrawn;

injecting a second portion of the plasma gel into the cavernosa of the patient.

2. The method of claim 1, wherein the blood sample is 36 ml.

3. The method of claim 1, wherein heating the isolated plasma comprises heating at 55-60° C. for 12 minutes to produce 12 ml of the plasma gel.

4. The method of claim 1, wherein the second portion of the plasma gel is 3 ml injected into the cavernosa with 1.5 ml injected directly into each of the left and right cavernosa along the length from base to glans.

5. The method of claim 4, wherein 1.5 ml of the second portion is injected into each of the left and right cavernosa.

6. The method of claim 1, further comprising injecting a third portion of the plasma gel into the submucosal space of the glans by making multiple small injections along the left and right sides of the glans.

7. The method of claim 6, wherein the third portion is 1.5 ml.

8. The method of claim 1, further comprises injecting a neurotoxin into the base and glans of the penis of the patient using a 30-gauge needle, wherein the neurotoxin is distributed in boluses; wherein the neurotoxin injected into the base comprises 200 units of abobotulinumtoxinA injected bilaterally into the subcutaneous tissues on the left and right sides of the penile base to relax the fundiform and suspensory ligaments.

9. The method of claim 8, wherein the neurotoxin injected into the glans comprises 100 units of abobotulinumtoxinA injected bilaterally into the subcutaneous tissues on the left and right sides of the glans.

10. The method of claim 8, further comprising performing penile stretching maneuvers following injection of the neurotoxin into the penile base to enhance distribution within the target muscles.

11. The method of claim 8, further comprising injecting the neurotoxin bilaterally into the base and proximal end of the corpus cavernosum, with 20 units injected into each of the left and right corpus cavernosum at the base of the penis and 20 units injected into each of the left and right proximal corpus cavernosum approaching the glans.

12. A method for penile rejuvenation, consisting of:
a) obtaining 36 ml of blood from a patient;
b) centrifuging the 36 ml of blood to isolate plasma at 1500× g for 10 minutes;
c) heating the isolated plasma at 55-60° C. for 12 minutes to produce 12 ml of plasma gel;
d) injecting 9 ml of the plasma gel into the subcutaneous plane above the deep Buck's fascia of the penile shaft by inserting a 30-gauge needle at the 6 and 9 o'clock positions along the penile shaft and distributing the gel as the needle is withdrawn;
e) injecting 3 ml of the plasma gel into the patient's cavernosa with 1.5 ml injected into each of the left and right cavernosa along the length from base to glans;
f) injecting 100 units of abobotulinumtoxinA using a 30-gauge needle into the base of the patient's penis on each side to relax the fundiform and suspensory ligaments; and
g) injecting 50 units of abobotulinumtoxinA botulinum toxin into each side of the glans of the patient's penis followed by massage or compression to assist with dispersion of the abobotulinumtoxinA within the glandular structure.

\* \* \* \* \*